United States Patent [19]

Suzuki

[11] Patent Number: 4,515,283
[45] Date of Patent: May 7, 1985

[54] BUNG FOR JARS

[76] Inventor: Hiro Suzuki, 109 Wicks Rd., North Ryde, N.S.W. 2113, Australia

[21] Appl. No.: 519,771
[22] PCT Filed: Nov. 15, 1982
[86] PCT No.: PCT/AU82/00188
§ 371 Date: Jul. 12, 1983
§ 102(e) Date: Jul. 12, 1983
[87] PCT Pub. No.: WO83/01767
PCT Pub. Date: May 26, 1983

[30] Foreign Application Priority Data
Nov. 13, 1981 [AU] Australia ............... PF1551
Jun. 2, 1982 [AU] Australia ............... PF4250

[51] Int. Cl.³ .............................................. A61M 1/00
[52] U.S. Cl. ..................... 215/270; 604/321; 215/296
[58] Field of Search ............. 604/317, 318, 319, 320, 604/321; 215/270, 260, 364, 309, 305, 295, 296

[56] References Cited
U.S. PATENT DOCUMENTS

| 801,734 | 10/1905 | Lorenz | 215/270 |
| 844,400 | 2/1907 | Radbruch | 215/364 |
| 1,566,983 | 12/1925 | Sheriff | 215/364 |
| 2,746,632 | 5/1956 | Bramming | 215/270 |
| 3,805,788 | 4/1974 | Kleiner | 604/320 |
| 3,843,016 | 10/1974 | Bornhorst et al. | 604/319 X |
| 3,874,541 | 4/1975 | Lagneaux | 215/364 X |
| 4,013,076 | 3/1977 | Puderbaugh et al. | 604/320 |
| 4,256,109 | 3/1981 | Nichols | 604/320 |

FOREIGN PATENT DOCUMENTS

| 155768 | 3/1954 | Australia | 215/364 |
| 247183 | 5/1966 | Australia | 215/305 |
| 366892 | 2/1932 | United Kingdom | 215/295 |

Primary Examiner—Donald F. Norton

[57] ABSTRACT

Aspirator apparatus including a jar and a bung for closing the mouth of the jar, the bung comprising a domed thermoplastic top provided with a peripheral skirt within the jar mouth and having an annular slot housing an O-ring providing a primary seal with the jar, the thermoplastic material of the bung being resilient to permit depression of the domed top with reduced pressure in the jar with resulting expansion of the skirt to provide a secondary seal between the inner end of the skirt and the jar.

6 Claims, 4 Drawing Figures

BUNG FOR JARS

This invention relates to bungs or stoppers for collection jars which are filled through the agency of a vacuum applied to the interior of the jar through the bung, provided with at least two orifices for the purpose.

BACKGROUND ART

Jars of this kind are usually composed of glass and prior forms of bungs therefor have comprised solid plugs of rubber, or similar material, within which metal adaptors for connection of lines are embedded. Good sealing under different degrees of vacuum have not always been maintained, and chipping of the glass jar by impaction with the metal adaptors has occurred. A common function of the jars is to trap aspirated fluids, or blood, flowing in a suction line inserted in a patient during surgical operations. Reliable operation of the jar and bung, and facility for quick change-over to a fresh jar, are of prime importance regardless of the operating vacuum, which may be varied in service.

It is a chief object of the invention to provide a bung for a collection jar which is reliable in operation under all operating vacuums, and is relatively inexpensive.

DISCLOSURE OF INVENTION

In accordance with a general form of the invention there is provided a bung for a collection jar moulded in shell-form from plastics material comprising an outwardly domed top, a peripheral skirt depending from said top, a circumferential recess in the outer face of said skirt, and a resilient O-ring accommodated within said recess, the moulding and shaping of said domed top and said skirt being such that with internal vacuum in said jar the domed top becomes depressed to flex said skirt outwardly against the jar to increase sealing between the jar and the bung.

BRIEF DESCRIPTION OF DRAWINGS

The invention will be described in more detail with reference to the accompanying drawings, in which.

BEST MODE OF CARRYING OUT THE INVENTION

Figure 1:
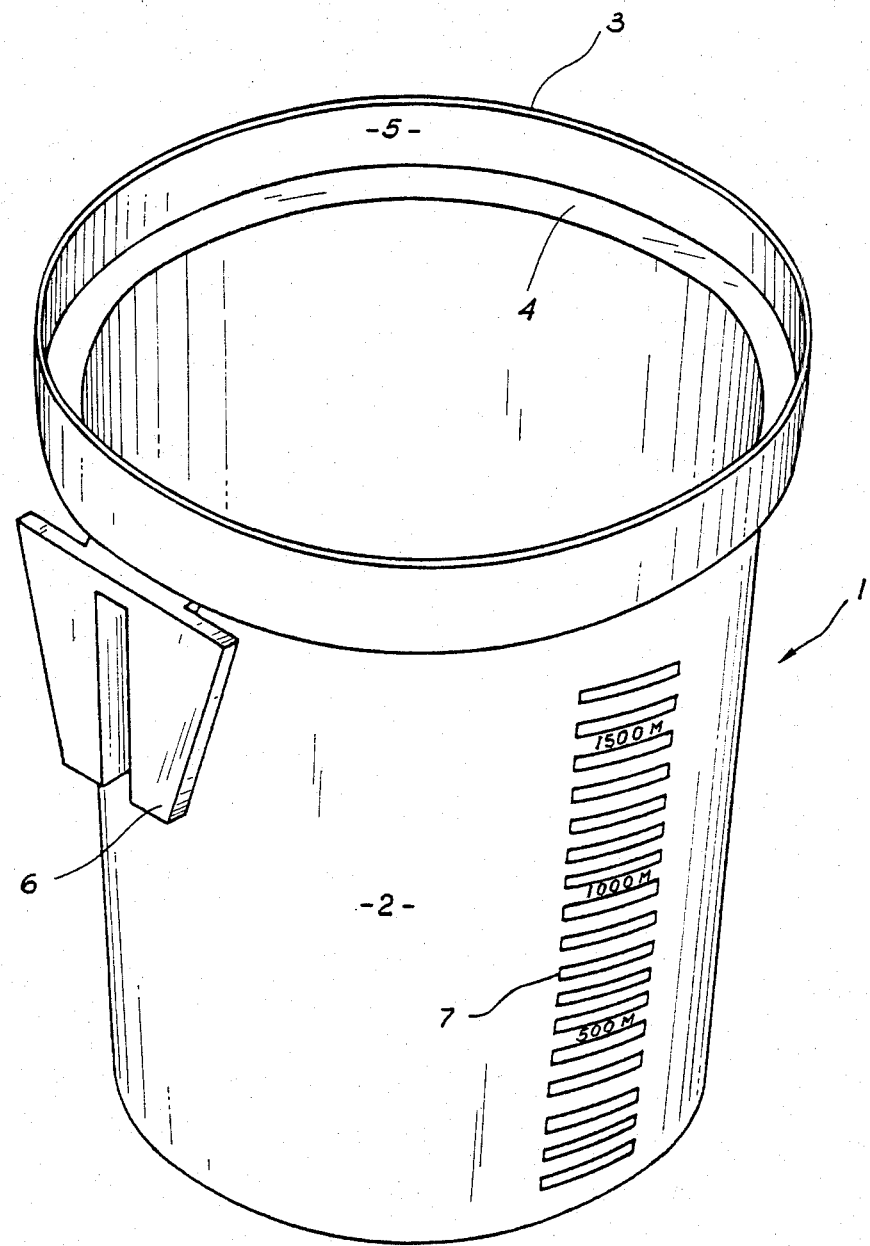
FIG. 1 is a perspective view of a typical jar to be utilised with the bung of this invention.

A jar 1 designed for use with the bung of the invention is shown in FIG. 1. Preferably it is composed of transparent polycarbonate and has a downwardly tapered wall 2 with an enlarged diameter mouth 3 connected to the wall 2 by a shoulder 4. The mouth 3 has an internal annular wall 5 which may be slightly downwardly converging. In its application as a trap jar for aspirated fluids during a surgical operation, the jar 1 will be conveniently located near the patient and may include a wedge-shaped key 6 engageable within a wall bracket for support of the jar. The key 6 is preferably integrally formed with the exterior of the wall 2. A graduated scale 7 may be embossed on the outer surface of the wall 2.

Figure 2:
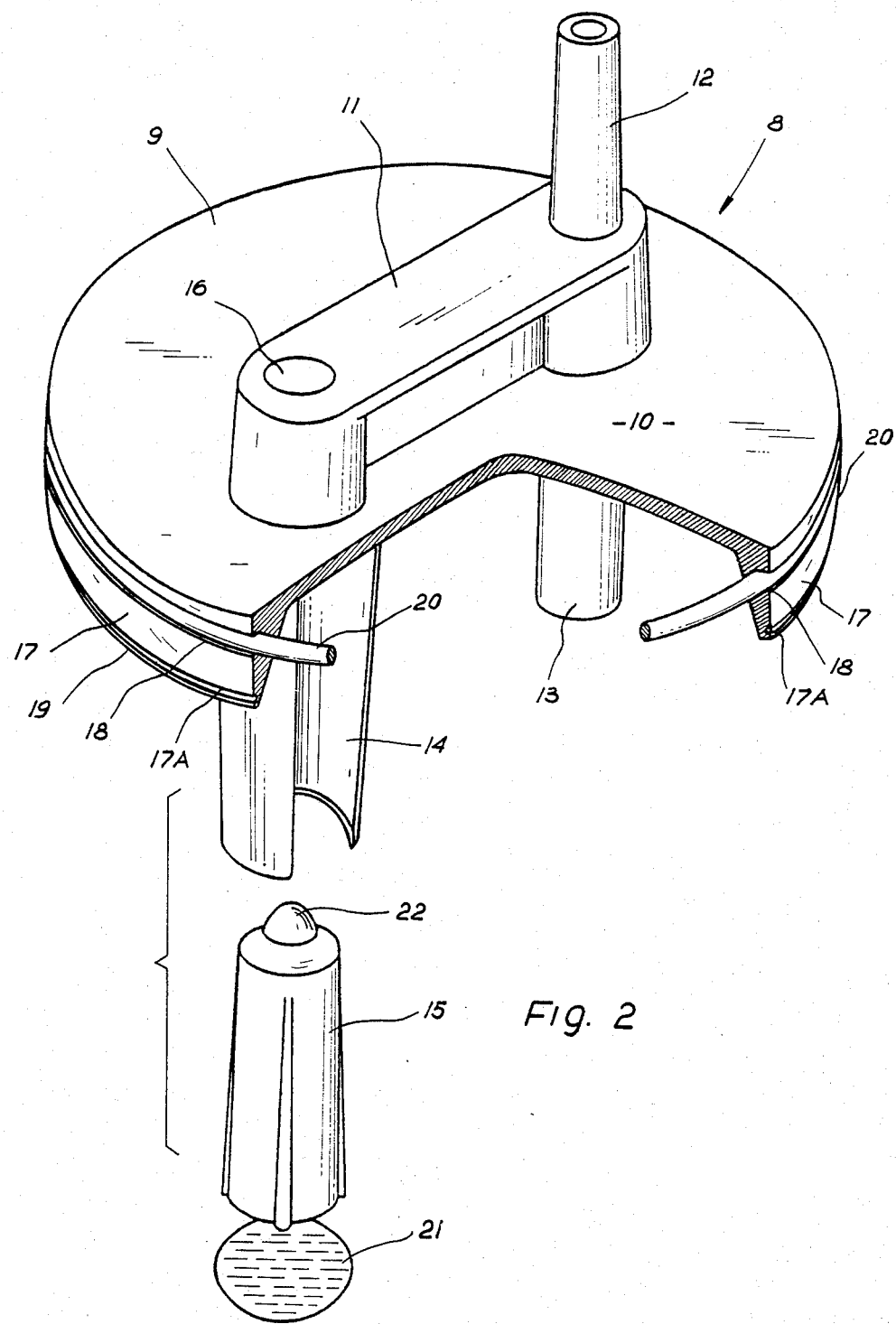
FIG. 2 shows in exploded perspective, and part section, a first embodiment of the bung.

A first form of bung 8 shown in FIG. 2 has a body 9 of shell-form composed of thermoplastic material provided with a top 10 on which is integrally formed a twisting handle 11 through which protrudes an inlet adapter 12 terminating at its lower end in an anti-splash tube 13. It is important that liquids drawn into the jar are not drawn away via the connecting vacuum line, and splashes of incoming liquids which could be drawn away are avoided through the tube 13 directing such liquid against the inner wall 2 of the jar 1. A split-cylindrical housing 14 for a float valve 15 held therein by a retaining disc 21 communicates through the twisting handle 11 with an orifice 16 for a vacuum line (not shown). The disc 21 is a snap-on fit on the end of the housing 14. An annular skirt 17 depends peripherally from the top 10 and is provided with an annular peripheral slot 18 in its outer wall. The skirt 17 also terminates externally in a small annular groove 17A adjacent its lower end 19 to render the region of the skirt 17 near its lower end 19 more pliable to enable it to conform under reduced pressure within the jar 1 to any irregularities in the internal surface in the mouth 3 of the jar 1 and thus achieve better-sealing. The moulding and shaping of both the domed top 10 and the skirt 17 will contribute to the improved seal by causing outward flexing of the skirt 17 against the mouth 3 of the jar 1. In one respect this is achievable by downwardly tapering the skirt, as shown in FIG. 2, and moulding with a resilient but reasonably stiff thermoplastic material, such as antistatic polypropelene. A diametral reinforcing rib (not shown) may be incorporated in the underside of the domed top 10 to ensure against flexing of the skirt 17 at too low a vacuum.

A resilient O-ring 20, serving as a primary seal, is accommodated within the annular groove 18. When in use the bung 8 is pressed into the mouth 3 to engage the primary seal of the O-ring 20 and tubing from the patient is attached to the inlet adaptor 12 and a vacuum line inserted into the orifice 16. The primary seal will be adequate for low vacuums, and when higher vacuums are applied the skirt 17 will automatically flex to provide a secondary seal. As the jar 1 fills with liquid the float 15 will rise until its valve head 22 engages a valve seat (not shown) internally surrounding the orifice 16 to close the suction line. By twisting handle 11 the bung 8 may be withdrawn and quickly fitted onto the mouth 3 of a fresh jar 1.

Under conditions of some high vacuum difficulty, sufficient to create a delay in change-over, can arise in removing the bung 8 from a full jar 1.

ALTERNATIVE EMBODIMENT

According to a second embodiment of the present invention, the annular groove 18 is composed of a recess 18A formed with two annular juxtaposed grooves 23 and 24. Preferably these two grooves 23 and 24 are separated by a downwardly inclined ramp 25. Furthermore, the uppermost groove 23; i.e., the groove closer to the top 10 is formed of an annulus of greater diameter than that of the groove 24.

Figure 3:
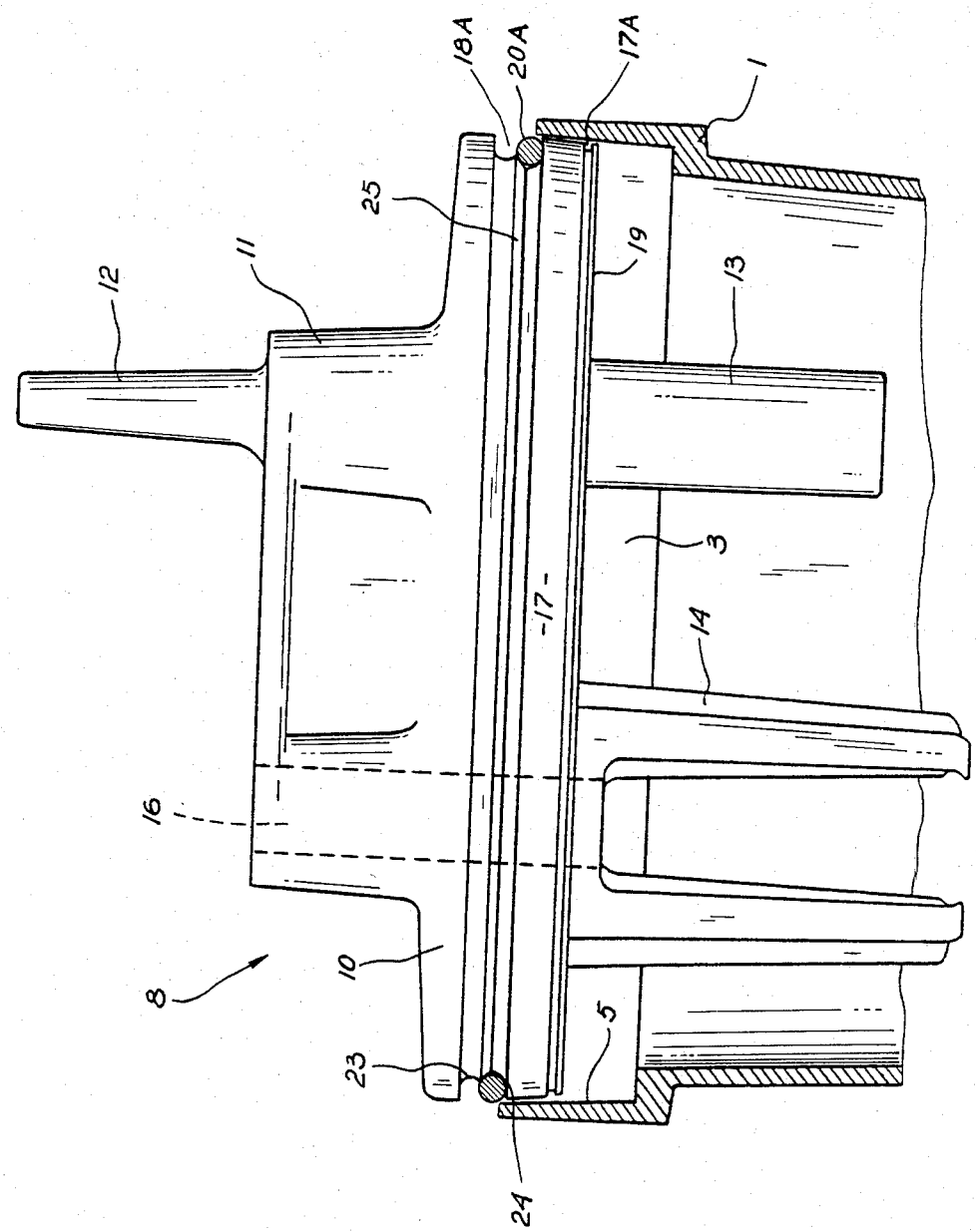
FIG. 3 shows in side elevation a second embodiment of the bung being entered into a jar shown in fragmentary section; and, FIG. 4 shows the bung of the second embodiment in its fully inserted position within the jar.
Figure 4:
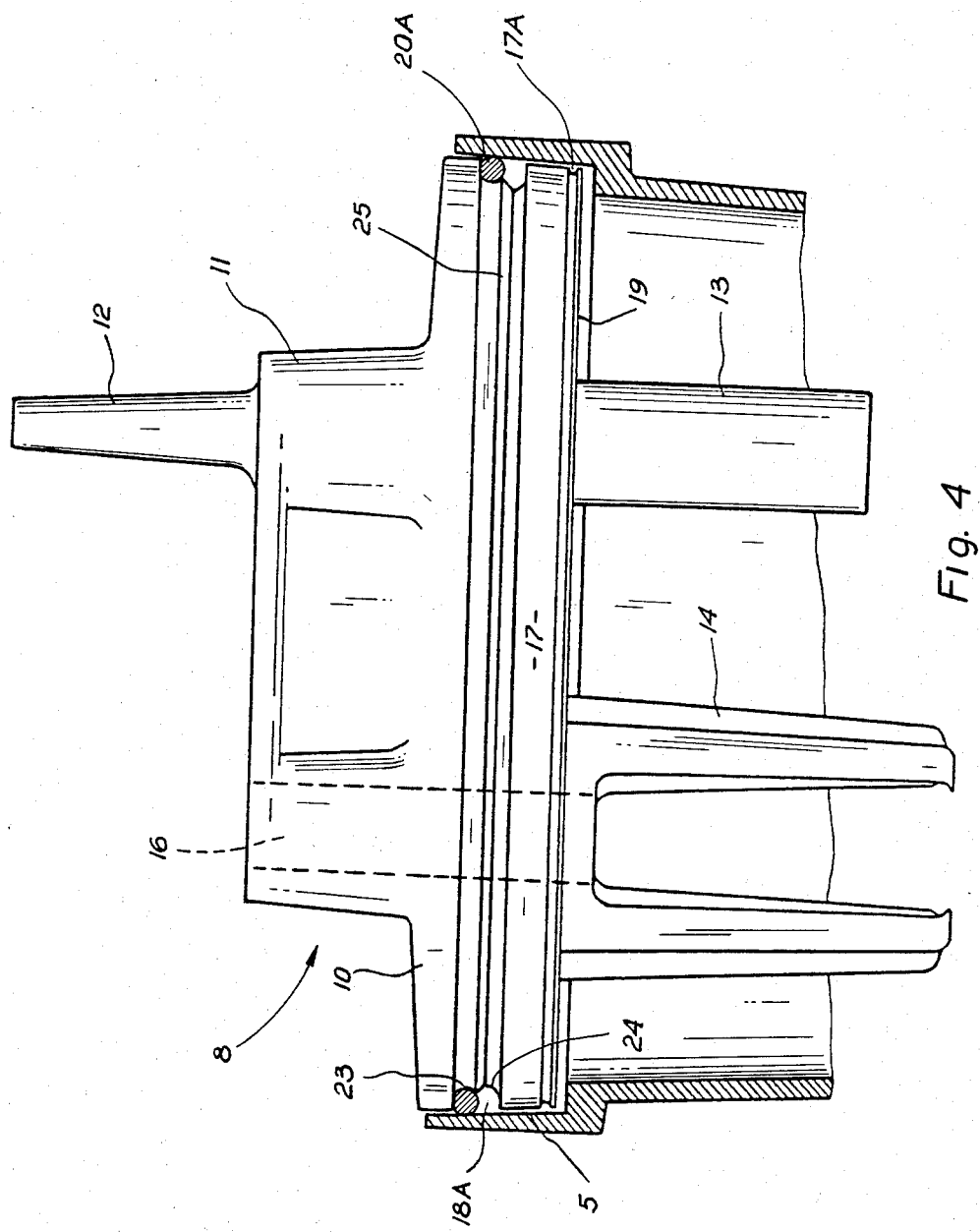

FIG. 3 shows the bung 8 being entered into the open mouth 3 of the jar 1 with an O-ring 20A located in the lowermost groove 24. The bung 8 may be forceably introduced into the mouth 3 of the jar 1, or placed just within the mouth 3 so that with evacuation of the interior of the jar 1 the bung 8 will be drawn down the tapering wall 5 onto the shoulder 4 inside the mouth 3 to the position shown in FIG. 4. In either instance friction between the O-ring 20A and the tapering inner wall 5 will cause the O-ring 20A to ride up and over the ramp 25 to become located within the groove 23. Being now in an annular groove of larger internal diameter than previously, the O-ring 20A will be pressed against the wall 5 with greater pressure. Furthermore, as previously described the domed top 10 of the bung 8 will be caused to flatten due to the reduced pressure within the jar 1 to further increase the sealing pressure through the O-ring 20A. Also, the lower end 19 of the skirt 17 will be caused to press against the internal wall 5 of the mouth 13.

When the bung 8 is required to be removed from the jar 1 finger pressure will be applied to the twisting handle 11 which will initially cause the O-ring 20A to pass down the ramp 25 into the annular groove 24 of smaller diameter. Accordingly, the sealing pressure between the bung 8 and the jar 1 will be reduced to facilitate removal of the bung 8 from the jar 1.

A preferred embodiment has been described in the foregoing passages but it should be understood that other forms, refinements and modifications are feasible within the scope of this invention.

I claim:

1. An aspirator apparatus comprising a collection jar having an open mouth and an internal shoulder joined to the mouth by a wall portion, and a bung closing said mouth and being moulded in shell-form from thermoplastic material, said bung comprising an outwardly domed top, a peripheral skirt depending from said top and being within said mouth and closely adjacent said wall portion, a circumferential recess in the outer face of said skirt, and a resilient O-ring accommodated within said recess and bearing against said wall portion to provide a primary seal between said jar and said bung, said apparatus includes the thermoplastic material of said bung being resilient to permit said domed top to depress inwardly with sub-atmospheric pressure within said jar to cause said skirt to press said O-ring and an inner end of said skirt against said wall portion to increase the sealing pressure between the jar and the bung.

2. A bung as claimed in claim 1, wherein thermoplastic material has resiliency and said skirt is downwardly tapered and has near its end an external annular slot, to render the inner end of said skirt more pliable.

3. A bung as claimed in claim 1, wherein a reinforcing rib is provided in the underside of said domed top to avoid depressing of said top except at relatively high internal vacuums.

4. A bung as claimed in claim 1, wherein a twisting handle for rotational removal of said bung is provided externally on said domed top.

5. A bung as claimed in claim 1, wherein said circumferential recess contains two juxtaposed annular grooves one below the other with the top-most groove being an annulus of greater diameter than the other, so that said O-ring, when normally seated in the lower groove by friction with said wall portion upon insertion of the bung into the mouth of the jar, is displaced into the upper groove to increase sealing pressure between said O-ring and the jar mouth, and as the bung is removed from the jar the O-ring becomes displaced back into the lower groove to relieve said sealing pressure to facilitate removal of said bung.

6. A bung as claimed in claim 5, wherein there is an inclined ramp between said two grooves to assist displacement of said O-ring from the lower groove to the upper groove.

* * * * *